(12) United States Patent
Mitchell

(10) Patent No.: US 8,361,004 B2
(45) Date of Patent: Jan. 29, 2013

(54) FOOT ABDUCTION APPARATUS

(76) Inventor: John R. Mitchell, Wayland, IA (US)

( * ) Notice: Subject to any disclaimer, the term of this patent is extended or adjusted under 35 U.S.C. 154(b) by 409 days.

(21) Appl. No.: 12/511,387

(22) Filed: Jul. 29, 2009

(65) Prior Publication Data

US 2011/0028876 A1 Feb. 3, 2011

(51) Int. Cl.
*A61F 5/00* (2006.01)
(52) U.S. Cl. ............................................... 602/29
(58) Field of Classification Search .............. 602/24, 602/29
See application file for complete search history.

(56) References Cited

U.S. PATENT DOCUMENTS

| | | | |
|---|---|---|---|
| 2,482,646 A | 1/1946 | Brachman et al. | |
| 2,906,261 A | 9/1959 | Craig | |
| 4,249,523 A * | 2/1981 | Bidwell | 602/24 |
| 4,303,065 A * | 12/1981 | Ericson | 602/24 |
| 4,336,795 A | 6/1982 | Nichols | |
| 4,412,536 A * | 11/1983 | Kurtz et al. | 602/24 |
| 4,481,940 A | 11/1984 | Kurtz et al. | |
| 4,520,803 A * | 6/1985 | Quest | 602/24 |
| 4,570,620 A * | 2/1986 | Kurtz et al. | 602/24 |
| 7,267,657 B1 | 9/2007 | Mitchell | |
| 7,569,023 B2 * | 8/2009 | Dobbs | 602/29 |
| 2007/0016122 A1 * | 1/2007 | Bowman | 602/24 |
| 2007/0289170 A1 | 12/2007 | Avent et al. | |

FOREIGN PATENT DOCUMENTS

WO WO2007112962 10/2007

* cited by examiner

*Primary Examiner* — Justine Yu
*Assistant Examiner* — Raymond E Harris
(74) *Attorney, Agent, or Firm* — Brett D. Papendick; Shuttleworth & Ingersoll, PLC

(57) ABSTRACT

An improved foot abduction apparatus allowing movement in a horizontal and vertical plane. The embodiments allow a user to more easily manipulate the apparatus in one or both planes through the use of strategically placed pivot points. The device utilizes at least one rigid member attached to coupling devices which contain at least one pivot point. The specialized coupling devices may be selectively attached to shoe receiving member or plates which are well known in the art. Additionally the shoe receiving members are able to receive an improved shoe containing a sole member contained with a silicone boot.

6 Claims, 8 Drawing Sheets

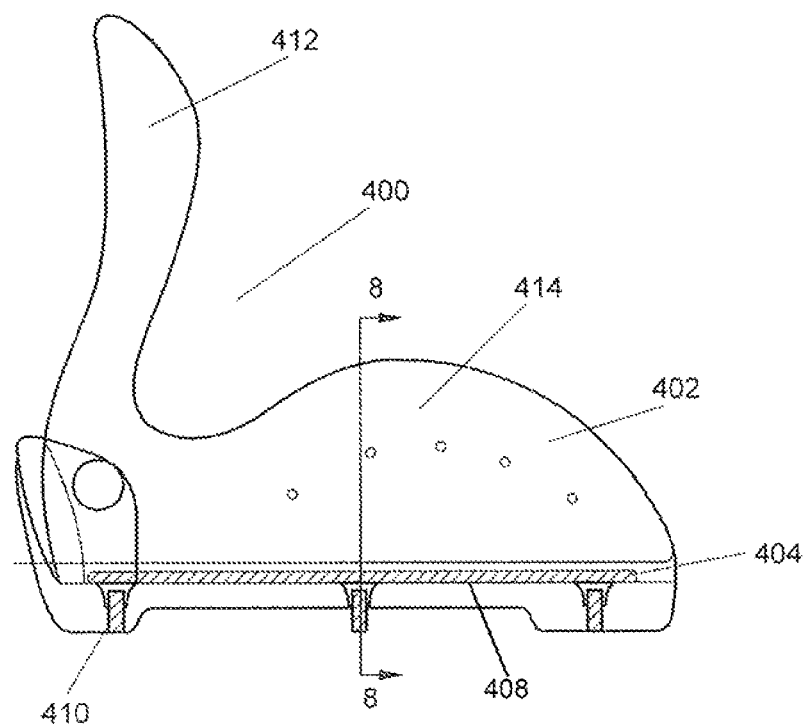
Fig. 7
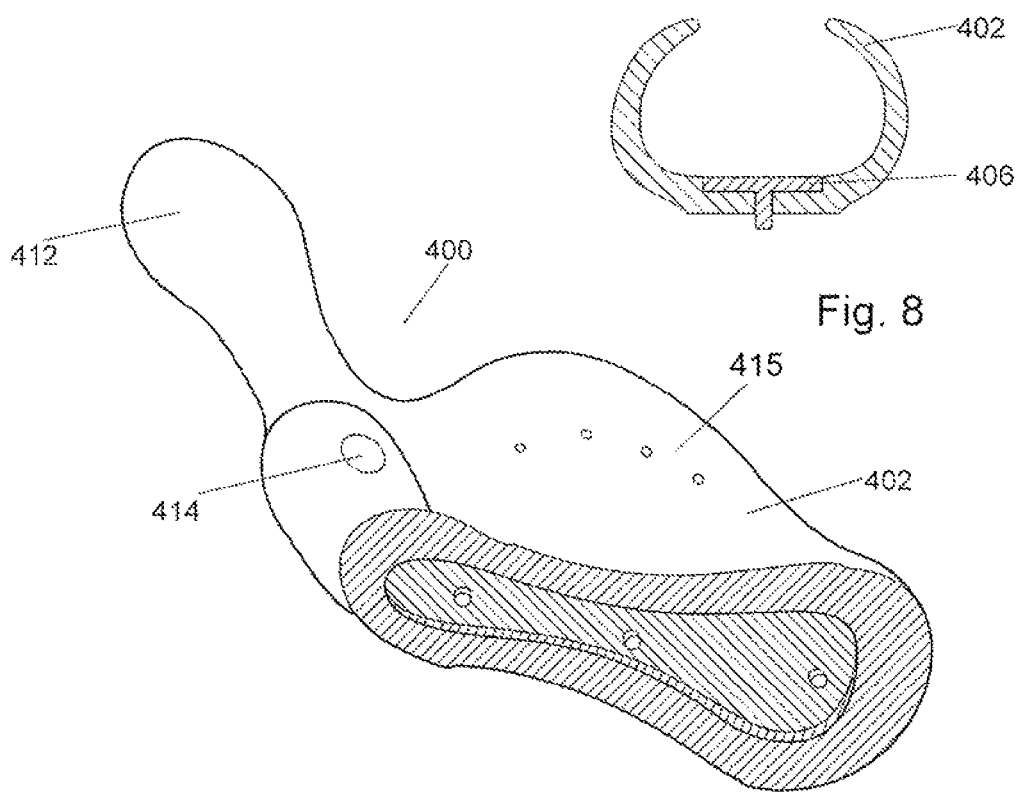
Fig. 8
Fig. 9 of the invention as it cushions the foot.

FOOT ABDUCTION APPARATUS

CROSS-REFERENCE TO RELATED APPLICATIONS

The present application claims priority to provisional patent application 61/034,450 which was filed on Jul. 29, 2008, and is hereby expressly incorporated by reference.

BACKGROUND

Dr. Ignacio Ponseti is an internationally famous physician and surgeon specializing in the treatment and management of a childhood deformity commonly know as a club foot. Dr. Ponseti has for many decades promoted the use of a foot and ankle abduction device, or orthosis, that is used to correct and prevent relapses of the club foot deformity. These abduction devices typically consist of a rigid bar connected between shoes worn by the child which bar separates the feet of the child and holds the feet in an outward rotation or abduction. Typically, if the condition is diagnosed early enough, this device is worn full-time for a period of months, but during the period of treatment, the angle of outward rotation is periodically adjusted.

The Ponseti technique, as it has become known throughout the world, has been highly successful in treating club feet without the necessity of corrective surgery. Many devices have been designed and used for many, many years in applying the Ponseti technique. Currently used devices that apply the Ponseti technique are shown in U.S. Pat. No. 7,267,657. In this patent, there are disclosed improvements in such devices which provide for quick release of the shoes from the abduction bar and which also provide a method for varying the abduction angle and locking it in place at a selected angle. Devices of this type have been extremely successful and are widely used by those who treat patients using the Ponseti technique. However, the devices allow the user limited movement in the horizontal and vertical planes. Typically the user must pivot on his or her feet to move forward or backward. Additionally, the rigid current foot abduction apparatuses make any movement difficult for the user. There is; therefore, a need for an improved orthosis that allows greater mobility in the horizontal and vertical planes for use in treating club feet and other gait issues using the Ponseti technique.

SUMMARY OF THE INVENTION

The improved abduction apparatus system for correcting gait issues allows the user, typically a patient with a club foot, greater mobility while wearing the brace. The at least two pivot points allow a greater range of movement in at least one of the horizontal and vertical planes. Several embodiments of the invention are possible to obtain the preferred result.

A first embodiment consists of a metal or plastic bar with connection means on the far sides of the bar. One coupling device is attached to each side of the metal bar and the coupling devices are pivotable in a vertical plane. Each coupling device is then attached to either a left footplate or a right footplate. The footplates are attached to the coupling device such that the angle of outward rotation may be periodically adjusted. The selected angle of outward rotation may be maintained once the footplate is firmly secured to the coupling device. The user of the foot abduction apparatus can lift up each foot in the vertical plane via the pivot point while maintaining the corrective angle of outward rotation. The user may achieve horizontal movement by manipulating the device in a "waddling" motion. The same embodiment also allows a user to more easily crawl if the user is unable to walk.

A second embodiment of the invention allows a user to manipulate the device in a horizontal plane. This embodiment consists of two rigid bars connected to coupling devices on both ends of the bars. The coupling device maintains the rigid members in parallel. Also attached to the coupling device are footplates which can receive a shoe. The rigid bars are attached to the coupling devices such that they are selectively pivotable at the point of connection. A user of the second embodiment attaches the shoes to the footplates. The user then manipulates the device by pushing one foot forward. The force causes the rigid bars to pivot allowing horizontal movement of the user's feet.

A third embodiment of the invention is similar to the first two and contains at least a second pivot point and an additional metal or plastic bar. The two bars are substantially in parallel and contain a means for attachment at each end. A connecting device is attached to each side of the bars. The bars may pivot about the coupling device in a horizontal direction while maintaining the bars in parallel. Each coupling device contains a third pivot point which may be attached to either a left footplate or a right footplate. The third pivot point allows movement in the vertical plane. Again the footplate contains a means to adjust and maintain the angle of outward rotation. A left shoe may then be attached to the left footplate and a right shoe attached to the right footplate. The user of this embodiment of the invention may simultaneously manipulate the device in a vertical and horizontal direction without the "waddling" motion associated with the first embodiment.

The coupling devices of the embodiments are preferably a one-piece plastic made from rotomolding or injection molding techniques. The attachments means may be of any of several know techniques for attachment but preferably the means is a standard screw. Additionally, the preferred embodiment contains a metal or rigid plastic base with means for attachment to the left or right footplate. The base is contained within a soft substance on all sides. The soft substance is preferably silicone rubber which allows greater comfort and reduces the potential of an allergic reaction to the wearer of the invention as it cushions the foot.

BRIEF DESCRIPTION OF THE DRAWINGS

FIG. 7 is a right side view of the shoe;

FIG. 8 is a cross-sectional view of the shoe taken at line 8;

FIG. 9 is a bottom perspective of the boot in which the rigid sole is inserted on the top of the silicone rubber;

DETAILED DESCRIPTION

Figure 1:
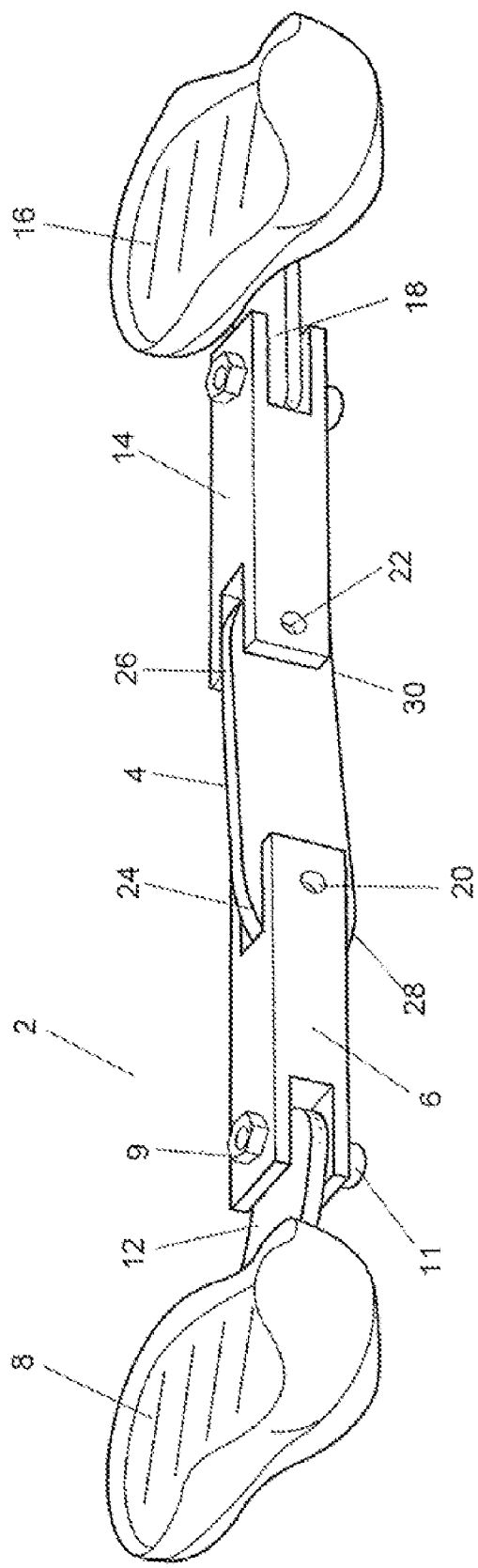
FIG. 1 is a perspective view generally from the top-rear of the invention showing the single bar embodiment.

Now referring to the drawings, FIG. 1 shows a single bar foot abduction system 2 comprising a rigid member 4, a first coupling device 6, a left shoe receiving member 8, a left plate 12, a second coupling device 14, a right shoe receiving member 16 and a right plate 18. The system 2 allows the user of the device to lift and lower each foot independently through a first pivot point 20 and a second pivot point 22.

The rigid member 4 may be comprised of a left rigid member 24 and a right rigid member 26. The left rigid member 24 and the right rigid member 26 substantially overlap one another and are housed in the bar adjuster device (not shown). The bar adjuster device allows the length of the overlap of the left rigid member 24 and the right rigid member 26 to be varied; thus, controlling the overall length of the rigid member 4. The greater the overlap of the left rigid member 24 and the right rigid member 26, the shorter the overall length of the rigid member 4.

The rigid member 4 further comprises a first end 28 and a second end 30. The first end 28 may be selectively attachable to the first coupling device 6 by several known methods; however, the preferred mode of attachment is by a nut and bolt (not shown in order to demonstrate shape of coupling device 6). The first coupling device 6 may then be selectively attachable to the left plate 12 by the preferred means of a nut 9 and bolt 11. The left plate 12 may then be attached to the left receiving shoe member 8. The angle of the left shoe receiving member 8 in relation to the rigid member 4 may be adjusted by loosening the attachment mechanism securing the first coupling device 6 to the left plate 12, manipulating the left plate 12 to the desired angle, and then retightening the attachment mechanism.

Figure 2:
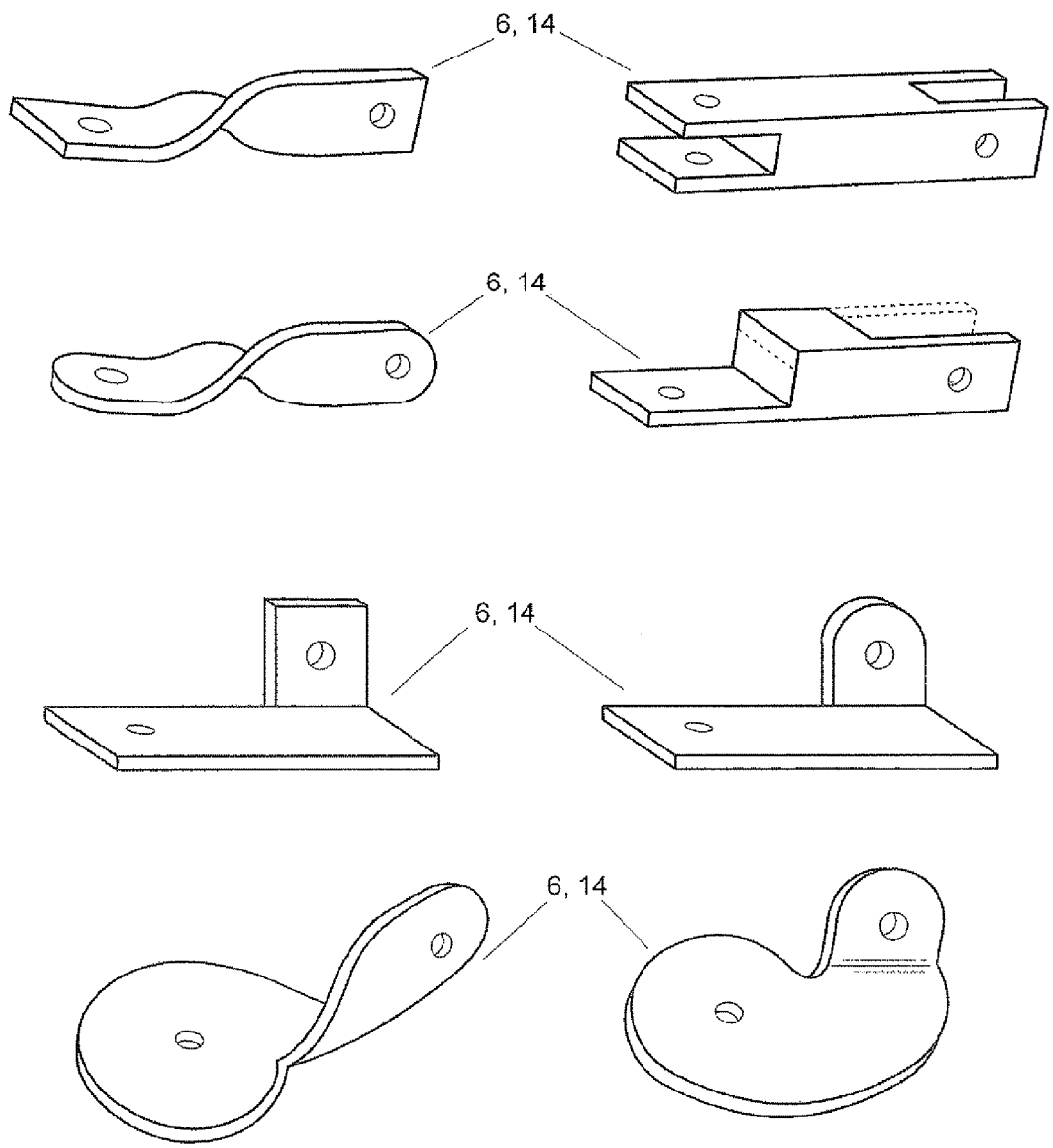
FIG. 2 is a perspective view of possible connecting devices for the invention.

The second end 30 may be selectively attachable to the second coupling device 14 in the same manner as the first end 28 is attached to the first coupling device 6. Similarly to the left plate 12 and its attachment to the first coupling device 6 and its attachment to the left shoe receiving member 8, the right plate 18 is selectively attachable to the second coupling device 14 and the angle between the right shoe receiving member 16 in relation to the rigid member 4 may be adjusted. Referring additionally to FIG. 2, the first coupling device 6 and the second coupling device 14 may be of a variety of configurations that allow movement in a vertical plane.

After the angle between the left shoe receiving member 8 and the rigid member 4, and the angle between the right shoe receiving member 16 and the rigid member 4 are set; the user inserts his left shoe and right shoe (neither shown) into the appropriate shoe receiving member 8 or 16. Once inserted, the shoes are held in place by any of several known attachment means including a snap-on means. As the user elevates or lowers his right foot, the rigid member 4 pivots about a first pivot point 20 located at the point where the rigid member 4 and the first coupling device 6 selectively attach. As the user elevates or lowers his left foot, the rigid member 4 pivots about a second pivot point 22 located at the point where the rigid member 4 and the second coupling device 14 selectively attach. The user may move in a horizontal direction by pivoting on the bottom of the left plate 12 or the right plate 18 in a shuffling type motion.

Figure 3:
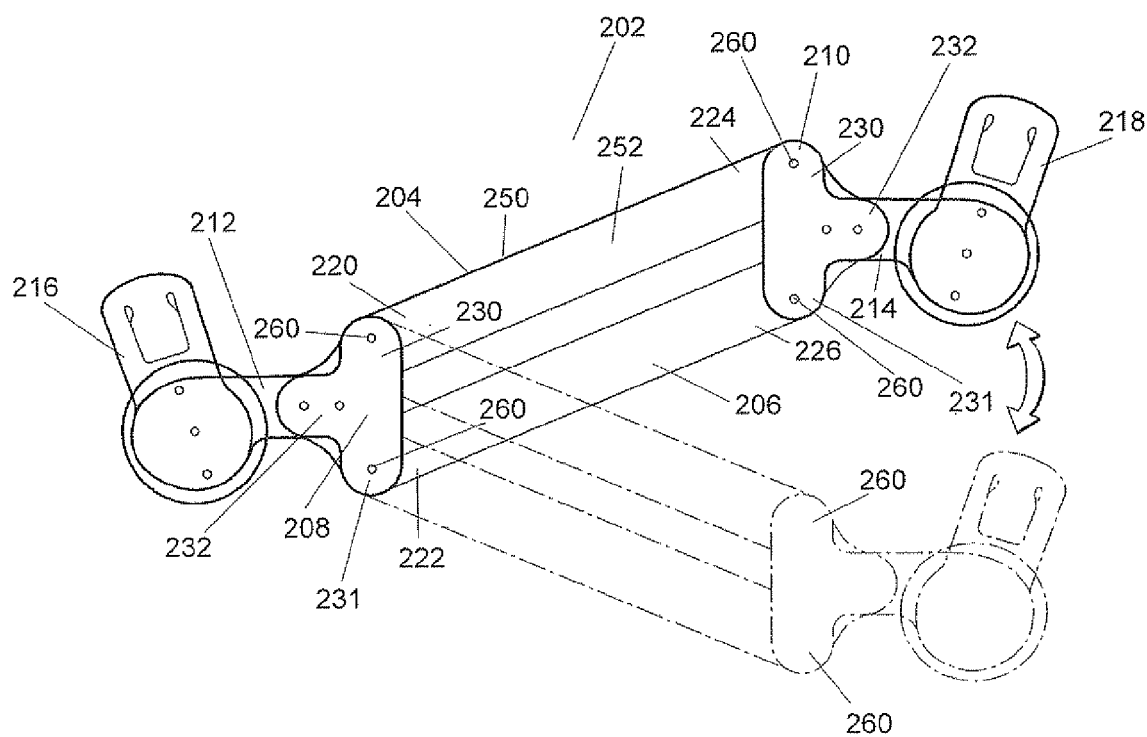
FIG. 3 is a top view of the double bar design without vertical movement.
Figure 4:
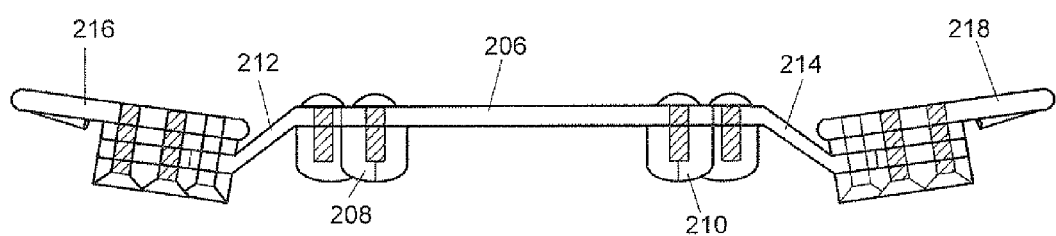
FIG. 4 is a side view of the double bar design without vertical movement.

Now referring to FIG. 3 and FIG. 4, a second embodiment of a foot abduction system 202 is detailed. The system 202 comprises a first rigid member 204, a second rigid member 206, a first coupling device 208, a second coupling device 210, a left plate 212, a right plate 214, a left shoe receiving member 216, and a right shoe receiving member 218. The first rigid member 204 and the second rigid member 206 lie within the same horizontal plane and are spaced such that they are substantially parallel with one another. Each rigid member 204, 206 are preferably made of metal or a rigid plastic and further comprise a first end 220, 222 respectively and a second end 224, 226 respectively. The first ends 220, 222 are selectively attachable to the first coupling device 208, while the second ends 224 and 226 are selectively attachable to the second coupling device 210.

The first coupling device 208 and the second coupling device 210 are preferably made of plastic and each further comprise three segments 230, 231, 232. The coupling devices are preferably made by rotomolding or injection molding techniques. The segment 232 is preferably substantially perpendicular to segments 230, 231. The segment 230 of the first coupling device 208 is selectively attachable to the first end 220 of the first rigid member 204; and the segment 230 of the second coupling device 210 is selectively attachable to the second end 224 of the first rigid member 204. The segment 231 of the first coupling device 208 is selectively attachable to the first end 222 of the second rigid member 206; and the segment 231 of the second coupling device 210 is selectively attachable to the second end 226 of the second rigid member 206.

Again referring to FIG. 3 and FIG. 4, the segment 232 of the first coupling device 208 is selectively attachable to the left plate 212. The means for attachment is preferably two standard screws. The segment 232 of the second coupling device 210 is selectively attachable to the right plate 214, again with a two screw attachment. Once each of the segments 230, 231, 232 of each coupling device 208, 210 are selectively attached, the preferred embodiment has the rigid members 204, 206, the left plate 212 and the right plate 214 in a position such that they remain in a fixed angle position. The first coupling device 208 and the second coupling device 210 may be located on an underside 250 of the rigid members 204, 206 or on an upper surface 252 of the rigid members 204, 206, although the preferred embodiment is on the underside 250 of the rigid member.

The left shoe receiving member 216 may be attached to the left plate 212 by a variety of known techniques including a screw. Similarly, the right shoe receiving member 218 is attached to the right plate 214. The left shoe receiving member 216 and the left plate 212 define an angle which may be adjusted and selectively fixed. The right shoe receiving member 218 and the right plate 214 define an angle which may be adjusted and selectively fixed. A shoe (not shown) may be of any of those well known in the art which have the capability of attaching to the left shoe receiving member 216 or right shoe receiving member 218. Additionally, the left plate 212 is preferably angled downward such that the bottom of the left shoe receiving member 218 is the same elevation as the bottom of the first coupling device 208 when the left plate 212 is attached to the left shoe receiving member 216 and the first coupling device 208. Similarly, the right plate 214 is preferably angled such that the bottom of the right shoe receiving member 218 is the same elevation as the bottom of the second coupling device 210 when the right plate 214 is attached to the right shoe receiving member 218 and the second coupling device 210.

The points at which the rigid members 204, 206 attach to the first coupling device 208 and second coupling device 210 define pivot points 260. The rigid members 204, 206 are pivotable upon the first coupling device 208 and the second coupling device 210. A user can then manipulate the device 202 in a first plane which would typically be the horizontal plane. As the user moves the right shoe receiving member 218 or the left shoe receiving member 216 in the horizontal plane, the rigid members 204, 206 pivot allowing horizontal movement. As the rigid members 204, 206 are substantially in parallel and there are at least four pivot points 260, the rigid members 204, 206 remain substantially in parallel with one another during operation. The horizontal movement is depicted by the first position of the device 202 evidenced by the dashed lines and the second position indicated by solid lines. Additionally, the fixed positions of the left plate 212 and the right plate 214 ensure the angle defined by the left plate 212 and the left shoe receiving member 216 remain constant as well as the angle defined by the right plate 214 and the right shoe receiving member 218 remain constant during operation of the system 202.

Figure 5:
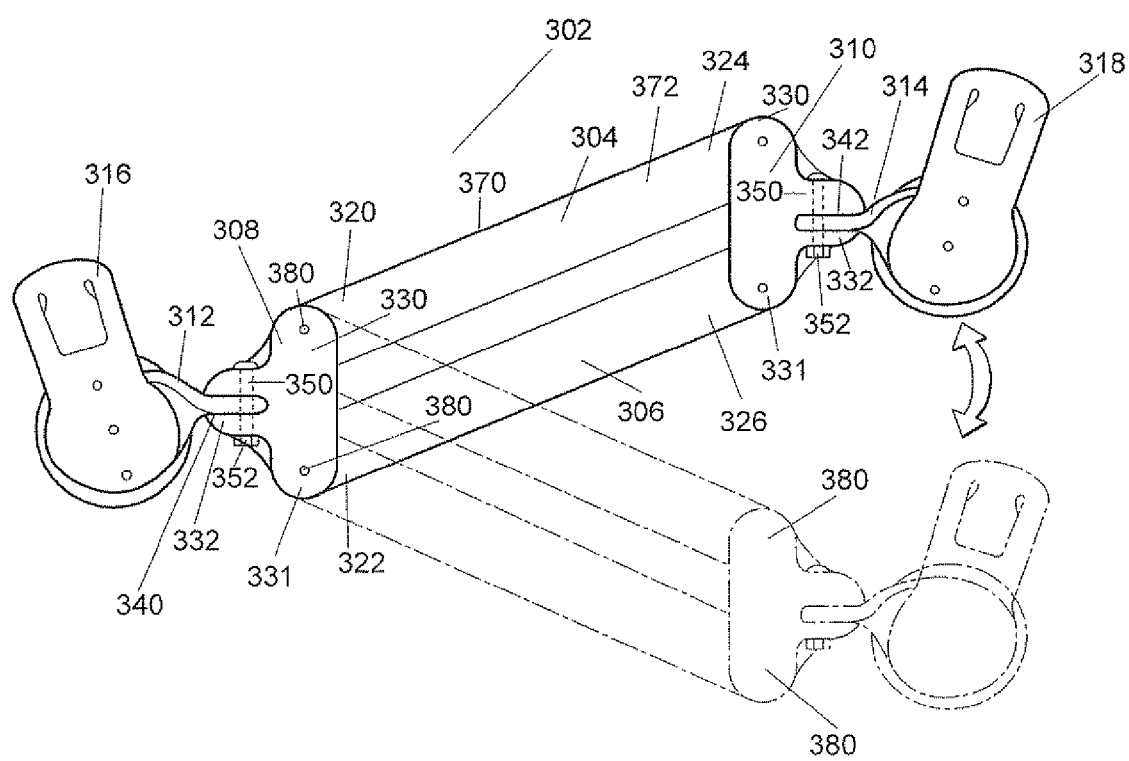
FIG. 5 is a top view of the double bar design with vertical movement.
Figure 6:
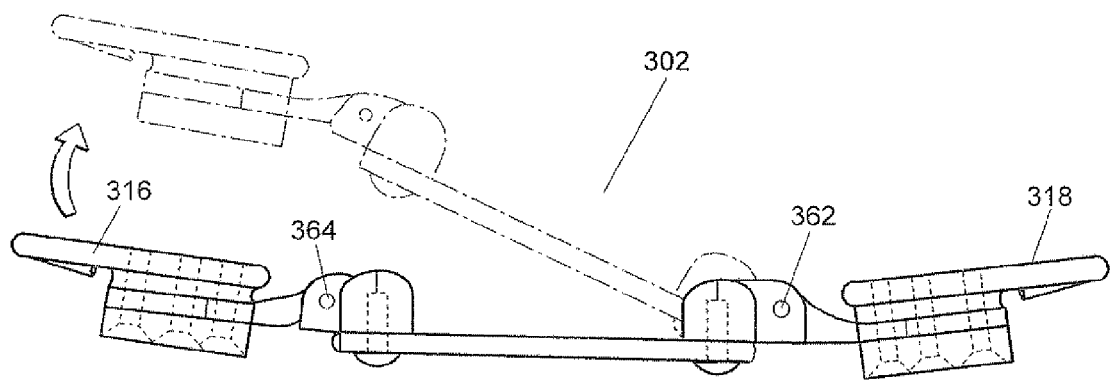
FIG. 6 is a rear view of the double bar design with vertical movement.

Now referring to FIG. 5 and FIG. 6, a third embodiment of a foot abduction system 302 is detailed. The system 302 comprises a first rigid member 304, a second rigid member 306, a first coupling device 308, a second coupling device 310, a left plate 312, a right plate 314, a left shoe receiving member 316, and a right shoe receiving member 318. The first rigid member 304 and the second rigid member 306 lie within the same horizontal plane and are spaced such that they are substantially parallel with one another. Each rigid member 304, 306 are preferably made of metal or a rigid plastic and further comprise a first end 320, 322 respectively and a second end 324, 326 respectively. The first ends 320, 322 are selectively attachable to the first coupling device 308, while the second ends 324 and 326 are selectively attachable to the second coupling device 310.

The first coupling device 308 and the second coupling device 310 are preferably made of plastic or metal alloy and each further comprise three segments 330, 331, 332. The coupling devices are preferably made by machining or injection molding techniques. The segment 332 is preferably substantially perpendicular to segments 330, 331. The segment 330 of the first coupling device 308 is selectively attachable to the first end 320 of the first rigid member 304; and the segment 330 of the second coupling device 310 is selectively attachable to the second end 324 of the first rigid member 304. The segment 331 of the first coupling device 308 is selectively attachable to the first end 322 of the second rigid member 306; and the segment 331 of the second coupling device 310 is selectively attachable to the second end 326 of the second rigid member 306.

Again referring to FIG. 5 and FIG. 6, the segment 332 of the first coupling device 308 is selectively attachable to the left plate 312. The segment 332 further comprises an elongated slot 340. The elongated slot 340 is of a size and shape which allows left plate 312 to slide within the confines of the elongated slot 340. The segment 332 of the second coupling device 310 is selectively attachable to the right plate 314. The segment 332 further comprises a slot 342 which is a size and shape which allow right plate 314 to slide within the confines of the slot 342. The attachment means for connecting left plate 312 to the first coupling device 308 or the right plate 314 to the second coupling device 310 is preferably a bolt 350 and a nut 352 or a screw pin (not shown). Once each of the segments 330, 331, 332 of each coupling device 308, 310 are selectively attached the preferred embodiment has the rigid members 304, 306, the left plate 312 and the right plate 314 in a position such that they remain in a fixed position to one another. The first coupling device 308 and the second coupling device 310 may be located on an underside 370 of the rigid members 304, 306 or on an upper surface 372 of the rigid members 304, 306, although the preferred embodiment has the coupling devices on the upper surface 372 of the rigid members 304, 306.

The left shoe receiving member 316 may be attached to the left plate 312 by a variety of known techniques including a screw. Similarly, the right shoe receiving member 318 is attached to the right plate 314. The left shoe receiving member 316 and the left plate 312 define an angle which may be adjusted and selectively fixed. The right shoe receiving member 318 and the right plate 314 define an angle which may be adjusted and selectively fixed. A shoe (not shown) may be of any of those well known in the art which have the capability of attaching to the left shoe receiving member 316 or right shoe receiving member 318. Additionally, the left plate 312 and the right plate 314 are preferably angled downward such that the bottom of the left shoe receiving member 316 and the right shoe receiving member 318 are the lowest elevation points of the device 302.

The points at which the rigid members 304, 306 attach to the first coupling device and second coupling device define pivot points 380. The rigid members 304, 306 are pivotable upon the first coupling device 308 and 310. A user can then manipulate the device 302 in a first plane which would typically be the horizontal plane. As the user moves the right shoe receiving member 318 or the left shoe receiving member 316 in the horizontal plane, the rigid members 304, 306 pivot allowing horizontal movement. As the rigid members 304, 306 are substantially in parallel and there are at least four pivot points 360, the rigid members 304, 306 remain substantially in parallel with one another during operation. Additionally, the fixed positions of the left plate 312 and the right plate 314 ensure the angle defined by the left plate 312 and the left shoe receiving member 316 remain constant as well as the angle defined by the right plate 314 and the right shoe receiving member 318 remain constant. The dashed lines of FIG. 5 indicate a first horizontal position while the solid lines indicate a second position.

In addition to movement in a horizontal plane, unique pivot points 362, 364 allow vertical movement as well. As a user lifts the left shoe receiving member 316, the right plate 314 pivots about pivot point 362 allowing vertical movement. Similarly, when the user lifts the right shoe receiving member 318, the left plate 312 pivots about pivot point 364 which allows vertical movement. The vertical movement is depicted in FIG. 6 in which a first position is shown by solid lines and a second position is shown by dashed lines. A user may manipulate the device in both the horizontal and vertical planes simultaneously. The pivot points 362 and 364 are always above the rigid members 304 and 306 during the normal operation of the system hereby limiting the range of motion of the left plate 312 and the right plate 314 such that the left plate 312 and the right plate 314 are prevented from becoming substantially inverted during operation of the system.

Now referring to FIG. 7, FIG. 8 and FIG. 9, a boot 400 which may be attached to the foot abduction apparatuses 2, 202, 302 detailed above is shown. The boot 400 comprises a flexible portion 402 and a rigid sole 404. Specifically referring to FIG. 8, a cross-sectional portion of the boot 400 is shown. A cavity 406 is formed within the flexible portion 402. The shape of the cavity 406 corresponds to the shape of the rigid sole 404. The rigid sole 404 is inserted into the cavity 406. Once in place, the flexible portion 402 surrounds a bottom surface 408 of the rigid sole 404. The flexible portion 402 is preferably made of silicone which possesses a cushioning characteristic. The cushioning characteristic allows the user of the boot 400 more comfort and greater shock absorption.

Again referring to FIG. 7, the rigid sole 404 is substantially planar. Once the rigid sole 404 is inserted into the cavity 406, attachment means 410 may be used to connect the boot 400 to the shoe receiving members described in the embodiments described above. Preferably, the attachment means 410 are standard screws that may be counter sunk in the rigid sole 404. Any number of attachment means 410 may be utilized, but the preferred embodiment has three attachment means 410.

The flexible portion 402 comprises a heel extension 412 which is at a substantial perpendicular in relation to the rigid sole 404. The heel extension 412 is shaped such that it conforms to a user's bank ankle, heel and lower back calf. The heel extension 412 also allows straps (not shown) to be connected to stabilize and support a user's foot and ankle. A heel hole 414 in the flexible portion 404 allows a doctor or parent to observe the placement of a user's ankle and heel to verify the correct positioning of the user's foot. Additionally, the flexible portion 402 comprises two flaps 415 which substantially cover the user's foot. The flaps 415 also allow straps to span the width of the shoe while protecting the user from the friction created by such straps.

Figure 10:
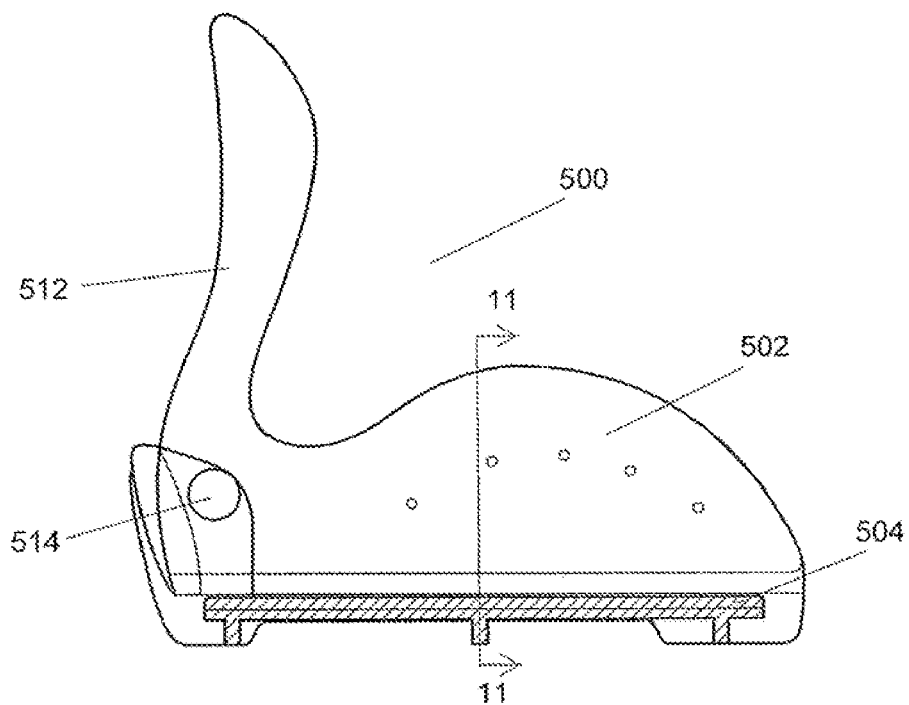
FIG. 10 is a right side view of the shoe.
Figure 11:
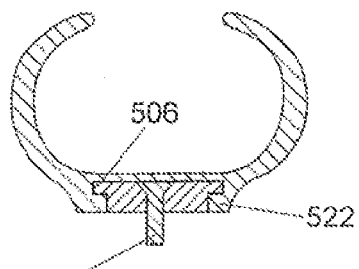
FIG. 11 is a cross-sectional view of the shoe taken at line 11.
Figure 12:
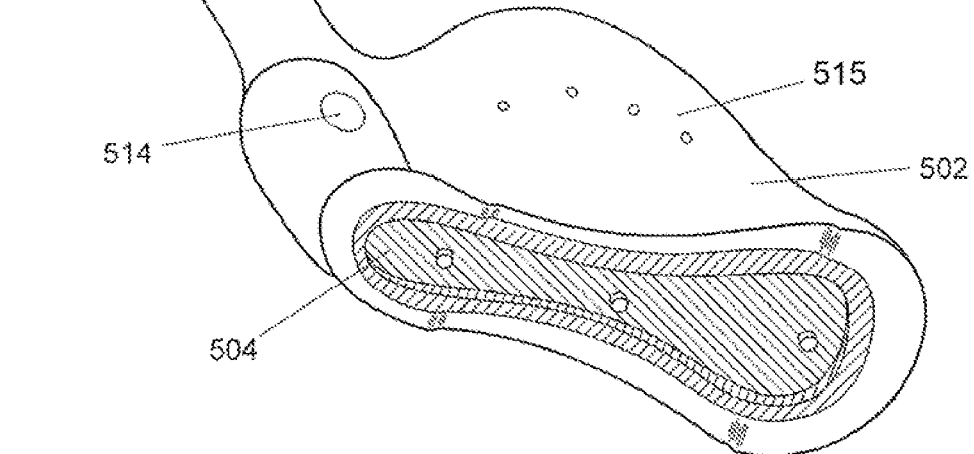
FIG. 12 is a bottom perspective of the boot in which the rigid sole is placed within the silicone.

Now referring to FIG. 10, FIG. 11 and FIG. 12 another embodiment of a shoe 500 for a foot abduction apparatus is detailed. The boot 500 comprises a flexible portion 502 and a rigid sole 504. Specifically referring to FIG. 8, a cross-sectional portion of the boot 500 is shown. A cavity 506 is formed within the flexible portion 502. The shape of the cavity 506 corresponds to the shape of the rigid sole 504. The rigid sole 504 is inserted into the cavity 506. The flexible portion 502 further comprises an edge 522 which is flexible. The cavity 506 and the edge 522 may be manipulated in such a way that the rigid sole 504 can be placed in the cavity 506. The edge 522 maintains the rigid sole 504 in the flexible portion 502. The flexible portion 502 is preferably made of silicone which possesses a cushioning characteristic. The cushioning characteristic allows the user of the boot 500 more comfort and greater shock absorption.

Again referring to FIG. 10, the rigid sole 504 is substantially planar. Once the rigid sole 504 is inserted into the cavity 506, attachment means 510 may be used to connect the boot 500 to the shoe receiving members described in the embodiments described above. Preferably, the attachment means 510 are standard screws that may be counter sunk in the rigid sole 504. Any number of attachment means 510 may be utilized, but the preferred embodiment has three attachment means 510.

The flexible portion 504 comprises a heel extension 512 which is at a substantial perpendicular in relation to the rigid sole 504. The heel extension 512 is shaped such that it conforms to a user's bank ankle, heel and lower back calf. The heel extension 512 also allows straps (not shown) to be connected to stabilize and support a user's foot and ankle. A heel hole 514 in the flexible portion 504 allows a doctor or parent to observe the placement of a user's ankle and heel to verify the correct positioning of the user's foot. Additionally, the flexible portion 502 comprises two flaps 515 which substantially cover the user's foot. The flaps 515 also allow straps to span the width of the shoe while protecting the user from the friction created by such straps.

Having thus described the invention in connection with the preferred embodiments thereof, it will be evident to those skilled in the art that various revisions can be made to the preferred embodiments described herein with out departing from the spirit and scope, of the invention. It is my intention, however, that all such revisions and modifications that are evident to those skilled in the art will be included with in the scope of the following claims.

What is claimed is:

1. A foot abduction system allowing vertical and horizontal movement comprising: a first rigid member comprising a first end and a second end, a second rigid member, a first coupling device, the first coupling device connected to the first end, the first coupling device containing a first pivot point, the first rigid member pivotable in a first plane about the first pivot point of the first coupling device, a first plate connected to the first coupling device, the first coupling device containing a second pivot point, the first coupling device comprises a first segment a second segment and a third segment, the first section comprises a means to attach the first plate to the first coupling device, the second section comprises a means to attach the first rigid member to the first coupling device, the third section comprises a means to attach the second rigid member to the first coupling device, the third segment substantially perpendicular to the first segment and the second segment, the first coupling device further comprising an elongated slot, the second pivot point within the elongated slot, the first plate having an end with a shape corresponding to the elongated slot wherein the end of the first plate can be inserted into the elongated slot, the first plate pivotable in a second plane about the second pivot point of the first coupling device, the second plane substantially perpendicular to the first plane, the first plate comprising a left shoe receiving member, a second coupling device, the second coupling device connected to the second end, the second coupling device containing a first pivot point, the first rigid member pivotable in the first plane about the first pivot point of the second coupling device, a second plate connected to the second coupling device, the second coupling device containing a second pivot point, the second plate pivotable in the second plane about the second pivot point of the second coupling device, the second plate comprising a right shoe receiving member.

2. The invention of claim 1 wherein:
the second pivot point always above the first rigid member during the normal operation of the system thereby limiting the range of motion of the first plate such that the first plate is prevented from becoming substantially inverted during operation of the system.

3. The invention of claim 2 wherein:
the second rigid member is connected to the first coupling device,
the first coupling device containing a third pivot point,
the second rigid member pivotable in the first plane about the third pivot point of the first coupling device,
the second rigid member is connected to the second coupling device,
the second coupling device containing a third pivot point,
the second rigid member pivotable in the first plane about the third pivot point of the second coupling device,
the first rigid member and the second rigid member are in parallel with one another.

4. The invention of claim 3 wherein:
the second coupling device comprises a first segment, a second segment and a third segment,
the first section comprises a means to attach the second plate to the second coupling device,
the second section comprises a means to attach the first rigid member to the second coupling device,
the third section comprises a means to attach the second rigid member to the second coupling device.

5. The invention of claim 4 wherein:
the first coupling device and the second coupling device are made from a thermoplastic,
the first coupling device and the second coupling device are made by the process of injection molding.

6. The invention of claim 4 wherein: the left shoe receiving member further comprising a left shoe adjustment mechanism, the left shoe adjustment mechanism for making angular adjustments, the right shoe receiving member further comprising a right shoe adjustment mechanism, the right shoe adjustment mechanism for making angular adjustments, an angle made between the right shoe receiving member and the left shoe receiving member, the angle capable of being maintained as the system is manipulated in the first plane and the second plane.

\* \* \* \* \*